United States Patent [19]

Doya et al.

[11] Patent Number: 4,459,423

[45] Date of Patent: Jul. 10, 1984

[54] PROCESS FOR PRODUCING α-AMINO ACIDS

[75] Inventors: Masaharu Doya; Takako Uchiyama, both of Niigata, Japan

[73] Assignee: Mitsubishi Gas Chemical Company, Inc., Tokyo, Japan

[21] Appl. No.: 355,142

[22] Filed: Mar. 5, 1982

[30] Foreign Application Priority Data

Mar. 26, 1981 [JP] Japan .................................. 56-44545
Mar. 27, 1981 [JP] Japan .................................. 56-44814

[51] Int. Cl.³ .......................................... C07C 51/06
[52] U.S. Cl. .................................... 562/559; 562/443; 562/444; 562/445; 562/507; 562/556; 562/557; 562/560; 562/561; 562/562; 562/563; 562/567; 562/570; 562/571; 562/573; 562/575
[58] Field of Search ............... 562/445, 443, 444, 553, 562/556, 559, 557, 574, 575, 507, 560, 561, 562, 563, 567, 570, 571, 573

[56] References Cited

U.S. PATENT DOCUMENTS 2,527,366 10/1950 Livak .................................. 562/575
4,243,814 1/1981 Pascal ................................. 562/575
4,272,631 6/1981 Schaaf ................................ 562/575

OTHER PUBLICATIONS

Kirk-Othmer Encyclopedia of Chemical Technology (3rd edition) vol. 2, p. 384 & 406.
CA 50, 9443.
CA 48, 7630.
Beilsteins Handbuch der Organische Chemie, 4th Edition, vol. 4, (1922) p. 343.
Chem. Abst., vol. 55, column 19798, 2nd Abstract, Oct. 2, 1961.

Primary Examiner—Michael L. Shippen
Attorney, Agent, or Firm—Cushman, Darby & Cushman

[57] ABSTRACT

A process for producing efficiently and economically without using strong acids nor strong bases, α-amino acids from α-amino acid amides by hydrolyzing α-amino acid amides in an aqueous medium in the presence of ammonia. If necessary, the resultant hydrolyzate liquid from which α-amino acid has been removed may be reused.

24 Claims, No Drawings

PROCESS FOR PRODUCING α-AMINO ACIDS

The present invention relates to a method for producing α-amino acids and more particularly it relates to a method for producing α-amino acids by hydrolysis of α-amino acid amides.

α-amino acids are important as intermediates for various industrial chemicals, additives for foods and fodders, and medicines.

Conventionally known methods for producing α-amino acids are, for example, (1) a method which comprises synthesizing α-aminonitrile from an aldehyde, hydrogen cyanide and ammonia, and hydrolyzing said α-aminonitrile with an alkali to obtain α-amino acid and (2) a method which comprises synthesizing hydantoin from sodium cyanide, ammonium bicarbonate and aldehyde, and hydrolyzing said hydantoin with an alkali to obtain α-amino acid.

However, these methods have the following defects: namely, since the hydrolysis step requires alkalis which are unrecoverable, raw material cost is high, and expensive anti-corrosion apparatuses are needed and furthermore since α-amino acids are obtained as alkali metal salts thereof, complicated desalting steps such as ion exchange resin treatments, fractional crystallization after neutralization with a strong acid, etc. are required to obtain free α-amino acids. Thus, they are industrially not satisfactory.

There are other methods for producing α-amino acids without strong acids or strong bases which have overcome the above defects. For example, "Beilstein IV" discloses in page 343 that aminoacetamide is boiled in the presence of water to obtain ammonia and glycine. However, according to our tracing tests, glycine was hardly obtained although ammonia and polypeptide were obtained. Thus, this method was found to be industrially of no use.

In order to overcome the defects of the conventional methods, the inventors have made intensive researches on efficient and industrially advantageous production of α-amino acids without using strong acids or bases.

As a result, it has been found that α-amino acids can be obtained in high yields without using strong acids or bases by hydrolyzing α-amino acid amides in the presence of ammonia and that the yield of α-amino acids can be further improved by reuse of reaction residue liquid which is the resultant α-amino acid amide hydrolyzate liquid from which α-amino acid has been removed (this will be referred to as merely "reaction residue liquid" hereinafter).

That is, the present invention relates to a method for producing α-amino acids wherein α-amino acid amides are hydrolyzed in an aqueous medium in the presence of ammonia and, if desired, the reaction residue liquid is reused.

The α-amino acid amides used in the present invention have no special limit, but generally those represented by the following general formula (1) can be practically advantageously used.

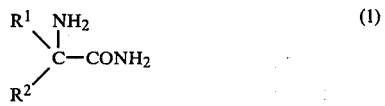

(wherein $R^1$ and $R^2$ which may be identical or different represent hydrogen atom, lower alkyl group, substituted lower alkyl group, cyclohexyl group, phenyl group or substituted phenyl group).

In the above general formula (1), the lower alkyl group includes straight-chain and branched-chain alkyl groups of 1–4 carbon atoms such as methyl, ethyl, propyl, isopropyl, butyl, iso-butyl, sec.-butyl, etc. The substituents in the above general formula (1) are, for example, hydroxy, methoxy, mercapto, methylmercapto, amino, carboxyl, carboxyamide, phenyl, hydroxyphenyl, guanidyl, etc.

Typical examples of the α-amino acid amides represented by the above general formula (1) are aminoacetamide, 1-methyl-aminoacetamide, 1-ethyl-aminoacetamide, 1-propylaminoacetamide, 1-isopropyl-aminoacetamide, 1-butyl-aminoacetamide, 1-isobutyl-aminoacetamide, 1-sec.-butyl-aminoacetamide, 1-phenyl-aminoacetamide, 1-cyclohexyl-aminoacetamide, 1-benzylaminoacetamide, 1-carboxymethyl-aminoacetamide, 1-aminomethylaminoacetamide, 1-methoxymethyl-aminoacetamide, 1-mercaptomethyl-aminoacetamide, 1-hydroxymethyl-aminoacetamide, 1-(β-carboxyethyl)-aminoacetamide, 1-(β-methylthioethyl)-aminoacetamide, 1-(α-hydroxyethyl)-aminoacetamide, 1-(β-aminoethyl)aminoacetamide, 1-(γ-carboxypropyl)-aminoacetamide, 1-(ω-guanidinopropyl)-aminoacetamide, 1-(ω-aminobutyl)-aminoacetamide, 1-(γ-hydroxy-ω-aminobutyl)-aminoacetamide and 1-(4'-hydroxybenzyl)-aminoacetamide. The α-amino acid amides used in the present invention may be those which are produced by any methods, but practically it is preferred to use α-amino acid amides or reaction product liquid containing the α-amino acid amides which are obtained by hydrolyzing α-aminonitriles using a small amount of a strong base material with keeping pH of reaction liquid at higher than 14 in the coexistence of a ketone because the decomposition degree to and selectivity of α-amino acid amides are both substantially 100%. This preferred method for producing α-amino acid amides used in the present invention will be explained in more detail. That is, amount of the strong base materials used is 0.01 mol or less per 1 mol of α-aminonitrile; the ketones are added to the reaction system so that pH of the reaction liquid exceeds 14; and the reaction temperature is kept at a relatively low temperature to carry out the reaction with keeping the pH of the reaction liquid at higher than 14. There is no specific limit in the starting materials α-aminonitriles, but generally those which are represented by the following general formula (2) are used.

(wherein $R^1$ and $R^2$ are as defined previously in the general formula (1) of the α-amino acid amides.)

Practically it is preferred that either one of $R^1$ and $R^2$ is hydrogen atom. Typical examples of α-aminonitrile represented by the general formula (2) are aminoacetonitrile, 1-methyl-aminoacetonitrile, 1-ethyl-aminoacetonitrile, 1-propyl-aminoacetonitrile, 1-isopropyl-aminoacetonitrile, 1-butyl-aminoacetonitrile, 1-isobutyl-aminoacetonitrile, 1-sec.-butyl-aminoacetonitrile, 1-phenylaminoacetonitrile, 1-cyclohexyl-aminoacetonitrile, 1-benzylaminoacetonitrile, 1-carboxymethyl-aminoacetonitrile, 1-aminomethylaminoacetonitrile, 1-methoxymethyl-aminoacetonitrile, 1-mercaptomethyl-aminoacetonitrile, 1-hydroxymethylaminoacetonitrile, 1-($\beta$-carboxyethyl)-aminoacetonitrile, 1-($\beta$-methylthioethyl)-aminoacetonitrile, 1-($\alpha$-hydroxyethyl)aminoacetonitrile, 1-($\beta$-aminoethyl)-aminoacetonitrile, 1-($\gamma$-carboxypropyl)-aminoacetonitrile, 1-($\omega$-guanidinopropyl)-aminoacetonitrile, 1-($\omega$-aminobutyl)-aminoacetonitrile, 1-($\gamma$-hydroxy-$\omega$-aminobutyl)-aminoacetonitrile, 1-(4'-hydroxybenzyl)-aminoacetonitrile, etc. The strong base materials may be organic or inorganic strong bases and practically preferred are alkali metal hydroxides such as sodium hydroxide and potassium hydroxide and organic quaternary ammonium compounds such as tetramethylammonium hydroxide, tetraethylammonium hydroxide and tetra n-propylammonium hydroxide. Amount of the strong base materials may be 0.01 mol or less per 1 mol of $\alpha$-aminonitrile, preferably 0.0001 to 0.01 mol, more preferably 0.001 to 0.01 mol.

There is no specific limit in the ketones added to the reaction system, and aliphatic and cycloaliphatic ketones are advantageously used. Typical examples are acetone, methyl ethyl ketone, diethyl ketone, methyl isopropyl ketone and cyclohexanone. These ketones are added to the reaction system until pH of the reaction liquid exceeds 14. Amount of the ketones may vary depending on kind and concentration of $\alpha$-aminonitriles, amount of the strong base materials, kind of carbonyl compounds, etc., in the reaction system. However, it is usually 0.1 to 10 mols per 1 mol of $\alpha$-aminonitrile.

When pH of the reaction liquid is not more than 14, the velocity of hydrolysis reaction of $\alpha$-aminonitrile decreases and thus amount of by-product $\alpha$-amino acid increases due to excess hydrolysis reaction and the strong base materials added as a catalyst are wasted. Therefore, the hydrolysis reaction discontinues before the hydrolysis degree reaches 100%.

Method for measurement of pH of reaction liquid has no particular limitation, but a pH meter with glass electrodes is generally used. Measurement of pH is generally effected on dilute acids or bases and hence range of pH to be measured by pH meter is ordinarily 0 to 14. Thus, pH of reaction liquids having a pH of 14 or less can be directly read from the pH meter, but pH of more than 14 cannot be directly read. Therefore, with reference to the reaction liquid having a pH or more than 14, the reaction liquid is diluted with a mixed liquid of water and ketone of the same composition ratio as water/ketone of the reaction liquid and pH of this diluted reaction liquid is measured by pH meter, to which a value $\log_{10}$ (dilution percentage) is added to obtain pH value of the reaction liquid. For example, when the reaction liquid is diluted to 10 times and 100 times, 1 and 2 can be added, respectfully, to the pH values which is read directly from pH meter.

Reaction temperature is preferably relatively low to keep pH of the reaction liquid at higher than 14 and usually is room temperature to normal temperatures, and at highest 40° C. Special heating or cooling is not needed.

Amount of water is at least 1 mol per 1 mol of $\alpha$-aminonitrile and preferably 1.5 to 10 mols per 1 mol of $\alpha$-aminonitrile.

Thus obtained reaction liquid contains only a very small amount of inorganic compounds such as strong base materials and contains substantially no unreacted $\alpha$-aminonitrile. Therefore, this reaction liquid as it is can be used as a starting material for production of amino acids.

There is no special limit in molar ratio of $\alpha$-amino acid amides to water in the reaction system. However, the smaller the molar ratio is, the higher the reaction velocity is and the less the side reaction is, but separation of the produced $\alpha$-amino acid from the reaction system requires a high energy. Thus, the molar ratio is preferably 0.001 to 0.1 mol per 1 mol of water.

Ammonia is usually added as ammonia water, but it may also be added as materials capable of producing ammonia or ammonium ion in the reaction system, e.g., ammonium bicarbonate, ammonium carbonate and other inorganic ammonium compounds. When the ammonia concentration in the reaction liquid is low, many side reactions occur and when it is high, the reaction velocity is low. Therefore, the concentration is generally at least 1% by weight, preferably 1 to 30% by weight. Of course, said concentration includes ammonia which is by-produced at the time of hydrolysis of $\alpha$-amino acid amides and dissolved in the reaction liquid.

The aqueous medium used in the present invention is usually water, but an organic solvent miscible with water may be present. Examples of the organic solvents generally used are aliphatic lower alcohols such as methanol, ethanol, propanol, etc. and ketones such as acetone, dioxane, etc.

Reaction temperature is ordinarily 50° to 250° C. but when the reaction temperature is low the reaction velocity is low and when it is high the side-reaction becomes vigorous. Thus, the reaction temperature is preferably 100° to 200° C.

Pressure used at the heating is ordinarily one which water, organic solvents, ammonia, etc. which are used in the reaction spontaneously produce, but may be optionally adjusted so as to keep liquid phase reaction system.

Separation of $\alpha$-amino acid from reaction liquid may be effected generally by crystallization of $\alpha$-amino acid. Crystals of $\alpha$-amino acid can be obtained by cooling the reaction liquid as it is or after having been concentrated or by adding thereto a poor solvent without subjecting the liquid to desalting. As the poor solvents, aliphatic lower alcohols such as methanol, ethanol, etc. may be advantageously used.

Reuse of thus obtained reaction residue liquid further improves yield of $\alpha$-amino acid. Said crystallization is usually carried out in a system different from the hydrolysis system. In this case the reaction residue liquid is reused by returning it to the hydrolysis system.

This mechanism is explained with reference to the case where aminoacetamide is hydrolyzed to obtain glycine. That is, the elementary reaction in this case is shown by

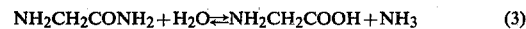

$$NH_2CH_2CONH_2 + H_2O \rightleftharpoons NH_2CH_2COOH + NH_3 \quad (3)$$

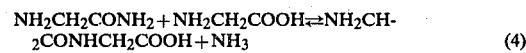

$$NH_2CH_2CONH_2 + NH_2CH_2COOH \rightleftharpoons NH_2CH_2CONHCH_2COOH + NH_3 \quad (4)$$

wherein (3) is the main reaction and (4) is a side reaction which are respectively reversible reactions and compositions of the products depend on compositions of the starting materials in the reaction liquid, temperature, etc. Therefore, it can be conjectured that it is one cause of the yield of $\alpha$-amino acid being further improved that the reaction of from left to right in (3) is accelerated and that of from left to right in (4) is restrained by the reuse of the reaction residue liquid.

When the reaction residue liquid is reused, α-amino acid amide, water and ammonia which are starting materials are replenished. All of or a part of the reaction residue liquid is reused. With increase of the number of times of reusing the reaction residue liquid the concentration of impurities in the reaction residue liquid increases and in this case it is desirable to stop the repeated reuse or to take a part thereof out of the system.

The process of the present invention may be carried out either in batch-wise or continuous manner.

According to the present invention α-amino acid can be produced efficiently and industrially advantageously without using strong acids or bases.

The following non-limiting examples will further illustrate the present invention.

EXAMPLE 1

In a 200 ml autoclave were charged 11.1 g of aminoacetamide and 100 g of 20% ammonia water and they were stirred and heated at 150° C. for 5 hours. It was found from the results of analysis of the reaction liquid after completion of the reaction by liquid chromatography that decomposition degree of aminoacetamide was 97.8% and yield of glycine was 91.3 mol %.

EXAMPLE 2

In a 200 ml autoclave were charged 4.4 g of 1-methyl aminoacetamide and 100 g of 5% ammonia water and they were stirred and heated at 125° C. for 8 hours. From the results of analysis of the reaction liquid after completion of the reaction by liquid chromatography it was found that decomposition degree of 1-methyl-aminoacetamide was 94.2% and yield of alanine was 87.8 mol %.

EXAMPLE 3

In a 200 ml autoclave were charged 3.7 g of 1-(β-methylthioethyl)-aminoacetamide and 100 g of 10% ammonia water and they were stirred and heated at 180° C. for 3 hours. From the results of analysis of the reaction liquid after completion of the reaction by liquid chromatography it was found that decomposition degree of 1-(β-methylthioethyl)-aminoacetamide was 96.4% and yield of methionine was 87.2 mol %.

EXAMPLE 4

In a 200 ml autoclave were charged 3.7 g of aminoacetamide and 100 g of 10% ammonia water and they were stirred and heated at 100° C. for 10 hours. From the results of analysis of the reaction liquid after completion of the reaction by liquid chromatography it was found that decomposition degree of aminoacetamide was 65.0% and yield of glycine was 58.9 mol %. Selectivity of glycine to the reacted glycineamide was 90.6%.

COMPARATIVE EXAMPLE

In a 200 ml three-necked flask provided with a thermometer, a stirrer and a reflux condenser were charged 3.7 g of aminoacetamide and 100 g of water and they were subjected to total reflux at 100° C. for 10 hours so that substantially no ammonia produced during the reaction was present in the reaction system. The results of analysis of the reaction liquid after completion of the reaction by liquid chromatography showed that decomposition degree of aminoacetamide was 58.9% and yield of glycine was 35.1 mol %. Selectivity of glycine to the reacted glycineamide was 59.6% which was much inferior to that of Example 4 where the same procedure as in this Comparative Example was carried out except that ammonia was present.

EXAMPLE 5

(A) In a 200 ml autoclave were charged 11.1 g of aminoacetamide and 100 g of 20% ammonia water and they were stirred and heated at 150° C. for 5 hours. After completion of the reaction the reaction liquid was taken out, concentrated and thereafter cooled to 5° C. The precipitated crystal was filtered out and washed with a small amount of cold water. This was dried to obtain 4.7 g of crystal having a glycine purity of 98.5% by weight.

20.3 g of reaction residue liquid was obtained. Composition of this reaction residue liquid was glycine 5.58 g, unreacted aminoacetamide 0.24 g, glycylglycine and others 0.67 g and the remainder water. Yield of glycine to the charged glycineamide was 90.8 mol %.

(B) All of the filtrate obtained above was charged in a 200 ml autoclave, and thereto were newly added 7.4 g of aminoacetamide and 100 ml of 20% ammonia water. They were again stirred and heated at 150° C. for 5 hours. After completion of the reaction, the reaction liquid was taken out and subjected to the same after-treatment as in (A) to obtain 5.9 g of dry crystal (glycine purity 98.7% by weight). 22.1 g of reaction residue liquid was obtained. The composition of this reaction residue liquid was glycine 6.8 g, unreacted aminoacetamide 0.32 g, glycylglycine and others 0.87 g and the remainder water. Yield of glycine to the newly added aminoacetamide was 94.0 mol %.

Successively, the same operation was repeated twice and as a result the yield of glycine to the charged glycineamide increased to 98.2 mol %.

EXAMPLE 6

(A) In a 200 ml autoclave were charged 8.8 g of 1-methyl-aminoacetamide and 100 g of 20% ammonia water and they were stirred and heated at 150° C. for 5 hours. After completion of the reaction, the reaction liquid was taken out, concentrated and then cooled to 5° C. The precipitated crystal was filtered out and washed with a small amount of cold water. This was dried to obtain 3.9 g of crystal having an alanine purity of 97.4% by weight. 19.5 g of reaction residue liquid was obtained. Composition of this reaction residue liquid was alanine 4.01 g, unreacted 1-methyl-aminoacetamide 0.51 g, alanylalanine and others 0.41 g and the remainder water. Yield of alanine to the charged 1-methyl-aminoacetamide was 87.8 mol %.

(B) The whole filtrate obtained hereinabove was charged in a 200 ml autoclave and thereto were newly added 4.4 g of 1-methyl-aminoacetamide and 100 ml of 20% ammonia water. Then, they were again stirred and heated at 150° C. for 5 hours. After completion of the reaction, the reaction liquid was taken out and subjected to the same after-treatments as in (A) to obtain 4.2 g of dry crystal (alanine purity 98.2% by weight). 20.3 g of reaction residue liquid was obtained. Composition of the reaction residue liquid was alanine 4.19 g, 1-methyl-aminoacetamide 0.59 g, alanylalanine and others 0.39 g and the remainder water. Yield of alanine to the newly added 1-methyl-aminoacetamide was 96.6 mol %.

EXAMPLE 7

(A) 112 g of 50% by weight aqueous aminoacetonitrile solution was charged in a 500 ml three-necked flask provided with a stirrer and a thermometer, to which 58 g of acetone and 5 ml of N-NaOH were added. They were stirred at 20° C. for 1 hour and then acetone in the reaction liquid was removed under reduced pressure to obtain 98 g of an aqueous aminoacetamide solution having the following composition. The pH value of the reaction liquid was 15.1 at the initiation of the reaction, then gradually decreased and was 14.5 at the end of the reaction.

Aminoacetamide 75.5% by weight (yield 100%)
Water and others 24.5% by weight (B) 9.8 g of thus obtained aqueous aminoacetamide solution and 100 g of 20% ammonia water were charged in a 200 ml autoclave and were stirred and heated at 150° C. for 5 hours. After completion of the reaction, the reaction liquid was taken out, concentrated and then cooled to 5° C. The precipitated crystal was filtered out and washed with a small amount of cold water. The crystal was dried to obtain 3.2 g of crystal having a glycine purity of 98.7% by weight.

13.7 g of reaction residue liquid was obtained and the composition thereof was glycine 3.71 g, unreacted aminoacetamide 0.14 g, glycylglycine and others 0.43 g and the remainder water. Yield of glycine to the charged aminoacetamide was 91.6 mol %.

(C) All of the filtrate obtained above was charged in a 200 ml autoclave. To this filtrate were newly added 9.8 g of an aqueous aminoacetamide solution obtained in the same manner as in (A) and 100 ml of 20% ammonia water. They we again stirred and heated at 150° C. for 5 hours. After completion of the reaction, the reaction liquid was taken out and subjected to the same aftertreatment as in (B) to obtain 4.8 g of dry crystal (glycine purity 98.8% by weight). 20.5 g of reaction residue liquid was obtained and composition thereof was glycine 6.01 g, unreacted aminoacetamide 0.23 g, glycylglycine and others 0.72 g and the remainder water. Yield of glycine to the newly added aminoacetamide was 93.9 mol %.

The same operation as above (C) was repeated twice to result in increase of yield of glycine to the charged aminoacetamide to 96.7 mol %.

We claim:

1. A process for producing an α-amino acid comprising hydrolyzing at 100° to 250° C. an γ-amino acid amide in an aqueous medium in the presence of ammonia at a concentration in the reaction liquid of at least 1% by weight.

2. A process according to claim 1 wherein the α-amino acid amide used in an α-amino acid amide represented by the general formula:

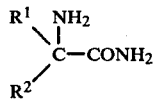

wherein $R^1$ and $R^2$ which may be identical or different represent hydrogen atom, lower alkyl group, substituted lower alkyl group, cyclohexyl group, phenyl group or substituted phenyl group.

3. A process according to claim 2 wherein $R^1$ and $R^2$ in the general formula are lower alkyl groups of 1 to 4 carbon atoms.

4. A process according to claim 2 wherein the substituents of the substituted lower alkyl groups and the substituted phenyl groups of $R^1$ and $R^2$ are hydroxy, methoxy, mercapto, methylmercapto, amino, carboxyl, carboxyamide, phenyl, hydroxyphenyl or guanidyl.

5. A process according to claim 1 wherein the α-amino acid amide is aminoacetamide, 1-methyl-aminoacetamide or 1-(β-methylthioethyl)-aminoacetamide.

6. A process according to claim 1 wherein the ratio of α-amino acid amide to water in the reaction system is 0.001 to 0.1 per 1 mol of water.

7. A process according to claim 1 wherein the aqueous medium is water or a mixture of water and an organic solvent miscible with water.

8. A process according to claim 8 wherein the organic solvent is an aliphatic lower alcohol or a ketone.

9. A process according to claim 7 where there is employed water alone as the aqueous medium.

10. A process according to claim 7 wherein there is employed a mixture of water and an organic solvent.

11. A process according to claim 1 wherein the reaction temperature is 100° to 200° C.

12. A process according to claim 1 including the step of reusing in the α-amino acid amide hydrolysis step the reaction residue liquid from the hydrolysis of the α-amino acid amide from which α-amino acid formed has been removed.

13. A process according to claim 12 wherein the α-amino acid amide is aminoacetamide, 1-methyl-amino-acetamide or 1-(β-methylthioethyl)-aminoacetamide.

14. A process according to claim 12 wherein the ratio of α-amino acid amide to water in the reaction system is 0.001 to 0.1 per 1 mol of water.

15. A process according to claim 12 wherein the aqueous medium is water or a mixture of water and an organic solvent miscible with water.

16. A process according to claim 12 wherein the reaction temperature is 100° to 200° C.

17. A process according to claim 1 wherein the temperature is 150° C.

18. A process for producing an α-amino acid comprising hydrolyzing at 100° to 250° C. an α-amino acid amide in an aqueous medium in the presence of ammonia and thereafter reusing in the α-amino acid amide hydrolysis step the reaction residue liquid from the hydrolysis of the α-amino acid amide from which α-amino acid formed has been removed.

19. A process according to claim 18 wherein the α-amino acid amide is amonoacetamide, 1-methyl-amino-acetamide or 1-(β-methylthioethyl)-aminoacetamide.

20. A process according to claim 18 wherein the ration of α-amino acid amide to water in the reaction system is 0.001 to 0.1 per 1 mol of water.

21. A process according to claim 18 wherein the aqueous medium is water or a mixture of water and an organic solvent miscible with water.

22. A process according to claim 21 wherein there is employed water alone as the aqueous medium.

23. A process according to claim 21 wherein there is employed a mixture of water and an organic solvent.

24. A process according to claim 18 wherein the reaction temperature is 100° to 200° C.

* * * * *